United States Patent [19]

Rice

[11] 4,314,821
[45] * Feb. 9, 1982

[54] SANDWICH IMMUNOASSAY USING PIEZOELECTRIC OSCILLATOR

[75] Inventor: Thomas K. Rice, White Bear Lake, Minn.

[73] Assignee: Minnesota Mining and Manufacturing Company, St. Paul, Minn.

[*] Notice: The portion of the term of this patent subsequent to Dec. 6, 1997, has been disclaimed.

[21] Appl. No.: 172,755

[22] Filed: Jul. 28, 1980

Related U.S. Application Data

[63] Continuation-in-part of Ser. No. 28,348, Apr. 9, 1979, Pat. No. 4,236,893.

[51] Int. Cl.³ .................... G01N 33/54; H01L 41/00
[52] U.S. Cl. ................................. 23/230 B; 23/915; 310/312; 324/71 R; 422/61; 424/12
[58] Field of Search ............... 23/230 B, 915; 424/12; 422/57, 61; 310/312; 324/71 R

[56] References Cited

U.S. PATENT DOCUMENTS 4,236,893 12/1980 Rice .................... 23/230 B

*Primary Examiner*—Sidney Marantz
*Attorney, Agent, or Firm*—Cruzan Alexander; Donald M. Sell; Carolyn A. Bates

[57] ABSTRACT

A method and kit for determining the total amount of an immunologically-reactive substance in a liquid sample containing interfering material capable of binding to an antigen. The method involves the steps of: (1) contacting a liquid sample containing or suspected of containing an antibody with the surface of a piezoelectric oscillator having a layer of antigen specific for the antibody attached thereto; (2) washing and drying the oscillator; (3) measuring the resonance frequency of the oscillator; (4) contacting said surface of the oscillator with a liquid reagent containing an excess amount of a substance specifically reactive with all of the antibody bound to the oscillator in step (1); (5) washing and drying the oscillator; and (6) measuring the change in resonance frequency of the oscillator form the first measurement whereby the amount of total antibody bound to the oscillator in step (1) is distinguished from the interfering material bound in step (1).

12 Claims, No Drawings ated to the amount of antibody in the sample by reference to a standard curve.

SANDWICH IMMUNOASSAY USING PIEZOELECTRIC OSCILLATOR

RELATED APPLICATION

This application is a continuation-in-part of my copending application Ser. No. 28,348, filed Apr. 9, 1979, now U.S. Pat. No. 4,236,893.

TECHNICAL FIELD

This invention relates to a method and article for the quantification of immunologically-reactive substances, e.g., antigens and antibodies, in a liquid sample. More particularly, it relates to a gravimetric assay for antigens or antibodies employing a piezoelectric oscillator having a layer for antigen attached to the surface thereof. The assay is uniquely designed for situations in which a significant amount of substances other than antibody attach to the antigen-coated oscillator along with the antibody.

BACKGROUND ART

A piezoelectric oscillator having a layer of an antigen attached to the surface thereof has been used for the direct measurement of the amount of a specific antibody in a liquid sample (Shons et al, *J. Biomed. Mater. Res.* Vol. 6, pp 565–570, 1972), and the indirect measurement of the amount of antigen in a liquid sample using competitive binding techniques (Oliveira et al, U.S. Pat. No. 4,242,096. In both methods, antibody in the liquid sample, specific for the antigen or to the surface of the oscillator, attaches to the oscillator. The change in resonant frequency of the oscillator due to the pick up of antibody can be correlated to the amount of antibody (direct assay) or the amount of antigen (competitive binding assay) present in the liquid sample by reference to a standard curve.

In my U.S. Pat. No. 4,236,893 it was disclosed that certain information regarding the make-up of the antibody layer attached to the antigen layer on the oscillator surface could be determined by adding a third (or sandwiching) layer of a particular substance. A substance was selected which would bind only to a particular class of antibody, e.g., IgG, IgM or IgE, etc., or to an antibody from a particular species, e.g., human, goat, rabbit, etc. The amount of substance which would bind to the antibody layer (as measured by the change in resonant frequency of the oscillator) could be directly correlated to the amount of the particular class or species of antibody present in the original liquid sample.

It has now been discovered that such a sandwiching assay can be used to determine not only the amount of a particular class or species of antibody present in the antibody layer, but also the amount of total antibody to a particular antigen present in the antibody layer. This is particularly useful in situations where the primary antigen layer picks up or binds extraneous substances in addition to antibody. In such a case, simply measuring the change in resonant frequency of the oscillator having two layers (antigen-antibody) bonded thereto would not provide an accurate determination of the amount of antibody in the original liquid sample since an unknown part of the frequency shift would be due to the nonspecific binding of extraneous substances. To overcome this problem, according to the present invention, a sandwiching layer comprising a substance which binds specifically to antibody is contacted with the oscillator to form a three-layered sandwich on the surface of the oscillator. The amount of substance bound in the sandwiching layer is directly related to the amount of antibody in the antibody layer. The actual quantity of antigen or antibody in the liquid sample can be determined by reference to a standard curve.

DETAILED DESCRIPTION

According to the present invention there is provided a method for determining the amount of an immunologically-reactive substance in a liquid sample comprising the steps of: (1) contacting a liquid sample containing or suspected of containing an antibody with the surface of a piezoelectric oscillator having a layer of antigen specific for the antibody attached to the surface thereof; (2) washing and drying the oscillator; (3) measuring the resonance frequency of the oscillator; (4) contacting the surface of the oscillator with a liquid reagent containing an excess amount of a substance specifically reactive with all of the antibody bound in step (1); (5) washing and drying the oscillator; and (6) measuring the change in resonance frequency of the oscillator from that obtained in step (3).

The method of the invention is desirably used in any situation where it is believed that a significant amount of nonspecific binding occurs in step (1) of the assay, i.e., where substances other than antibody are picked up and contribute to any frequency shift observed in step (3). By adding the sandwiching layer, only that portion of the frequency shift contributed by antibody binding is determined.

The assay may be used for direct measurement of antibody or indirect measurement of antigen using competitive binding techniques. In the latter assay, a predetermined amount of antibody is added to the liquid sample in step (1). The antigen immobilized on the oscillator and the free antigen in the sample compete for binding sites on the antibody. The amount of antibody which binds to the oscillator is inversely proportional to the amount of antigen in the sample.

Although the sandwich assay of the present invention is useful whenever nonspecific binding to the primary antigen layer occurs, it is especially suitable for the quantification of small (molecular weight less than about 10,000) molecules (antigens) using competitive binding techniques. In such assays, nonspecific binding appears to present the greatest problem.

The equipment needed to carry out the assay includes a piezoelectric oscillator and an instrument for measuring the resonance frequency of the oscillator. Piezoelectric oscillators are commonly used in electronic equipment or clocks as frequency standards and controllers. Generally, they consist of a small quartz wafer (or other material), having metal electrodes deposited on either side and some means provided for making electrical contact with an oscillator circuit. When placed in such a circuit, the portion of the wafer located between the electrodes vibrates with the precise natural frequency of the wafer. A given mass coupled to the electrode of the oscillator or crystal (used interchangeably herein) causes a decrease in the initial frequency of the crystal in an amount proportional to the mass added.

Shons et al, supra, describe a direct method for measuring the amount of an antibody in a liquid sample using a piezoelectric quartz crystal. The crystal is first coated with the antigen specific for the antibody being assayed and its frequency measured. The coated crystal is then exposed to the sample containing the antibody.

The change in frequency of the crystal due to antibody pickup is a direct measurement of the amount of total antibody in the sample.

An indirect method for determining the amount of an antigen in a liquid sample is disclosed by Oliveira et al, supra. A piezoelectric oscillator having an antigen adsorbed on the surface thereof is exposed to a sample containing the antigen and a predetermined amount of antibody specific for the antigen. The antigen attached to the crystal competes with the antigen in the sample for the supply of antibody. The change in frequency of the piezoelectric oscillator is compared to a standard curve, and the actual amount of antigen in the sample is determined.

The assay techniques of Shons et al and Oliveira et al are quite accurate for measuring the amounts of antibody and antigen, respectively, in situations where virtually all of the protein attached to the primary antigen layer is the antibody being measured. However, if a significant amount of extraneous substances attach to the oscillator, inaccurate measurements result. The present invention provides several steps beyond the assays of Shons et al and Oliveira et al which overcome the effects of nonspecific binding to the primary antigen layer.

The procedure for preparing the oscillators for use according to the method of the invention is described by Oliveira et al, supra, the disclosure of which is incorporated herein by reference.

Basically, the antigen may be attached to the oscillator by a number of conventional techniques known in the art for attaching proteins to solid supports. The antigen may simply be allowed to adsorb from an aqueous solution onto the surface of the oscillator. This method is least preferred because it contributes to a relatively high degree of nonspecific binding during the assay, and sensitivity is reduced.

Another technique for depositing the antigen on the oscillator is by crosslinking the protein antigen with a conventional agent such as glutaraldehyde.

Antigens may also be bound to the oscillator by first applying a priming coat. Antigens may be deposited on hydrophobic polymer-coated oscillators (such as polystyrene or fluorinated polymers) in which case attachment occurs by dispersion force interaction. One disadvantage with this method is that it may contribute to nonspecific binding when the surface is exposed to additional proteins, for example, during the assay.

Similarly, priming materials such as gum arabic, which bind to proteins through anionic interactions, may be used.

An especially preferred class of priming agents for the attachment of the antigen to the oscillator is described in U.S. Pat. No. 4,210,722 assigned to the assignee of the present application and also incorporated herein by reference. These priming agents are polymers, preferably poly(2-hydroxy-3-dimethylamino-1,4-butane) which, when applied to the surface of the oscillator, promote the deposition of a uniform layer of antigen on the oscillator. Nonspecific adsorption during the assay is minimized and a high degree of sensitivity is achieved.

The antigen is immobilized or adsorbed on the oscillator (treated or untreated) by exposing the oscillator to an aqueous solution of the antigen. A simple antigen may be present in the solution, or the antigen may consist of a complex mixture of molecules. Optimum concentration for attachment (or adsorption) varies from antigen to antigen according to their solubility or molecular weight. However, concentrations in the range of 0.1 to 100 milligrams per milliliter are generally preferred. Attachment is preferably accomplished at room temperature and at a pH which maintains the biological activity of the antigen. Optimum time for the attachment of antigens to the oscillator varies with the molecular weight and polarity of the antigen.

Before removing the oscillator from the antigen solution, a water wash is directed into the solution and the oscillator is thoroughly washed without contacting the air. This wash procedure prevents contact of the oscillator with denatured protein at an air-protein solution interface. The oscillator is removed and allowed to dry. The frequency of the coated oscillator is then determined. The oscillator is ready to be used in an immunochemical assay.

The antigen-coated oscillator is stable and may be stored for extended periods of time (e.g., several months) without loss of immunological activity.

To assay for the amount of antigen or antibody in a liquid sample, the liquid sample is applied to the antigen-coated crystal surface. This may be accomplished either by immersion of the crystal in the liquid sample or by application of the liquid sample to a single side of a crystal. If a single side of an oscillator is used the other side may be separately employed for a subsequent assay. The crystal may be incubated at temperatures preferably between 4° and 37° C. and for a period preferably ranging from 15 minutes to 24 hours. In order to assay for the amount of antigen in the liquid sample, a predetermined amount of antibody must be added to the sample prior to contacting the sample with the surface of the oscillator.

After the oscillator is washed and dried, its resonance frequency is measured. If one desires to quantify the total amount of protein picked up by the oscillator, it is also necessary to measure the resonance frequency of the oscillator immediately prior to contacting the oscillator with the liquid sample and compare it to a standard curve. If one is satisfied that the change in frequency is due exclusively to the binding of antibody, the assay is concluded. However, if the change in frequency is due, in part, to the binding of other substances to the crystal, a sandwiching layer is applied to determine how much antibody is bound to the crystal. A solution containing an excess amount of a substance specific for the antibody such as an anti-antibody is applied to the crystal surface in the same manner and under the same circumstances described above for the assay of the unknown liquid sample. By "excess" amount is meant an amount in excess of that which would completely saturate the binding sites available in the antibody layer. This amount is readily determined using standard titration techniques. The substance used to form the sandwiching layer may be any substance that binds specifically to the antibody being measured. The preferred binding substance is an anti-antibody obtained in the conventional manner from sera of a species immunized with the antibody from another species, e.g., sheep anti-rabbit IgG. If all of the antibody available to bind to the primary antigen layer is known to be of a certain class, e.g., IgG, substances such as Protein A or a lectin specifically reactive with that class of antibody may be used.

After incubation with this antibody-specific material, the oscillator is washed and dried and its resonance frequency is measured. From this reading and the past frequency, a change in reading due to the added mass of the newly-attached antibody-specific substance is calculated. This resultant change in resonance frequency ($\Delta Hz$) may be interpreted in any of a number of ways. Firstly, it may be taken as a qualitative indication that some antibody was bound in the primary assay. Secondly, by comparison to assays run with predetermined amounts of a given antigen or antibody, the actual amount of antigen or antibody in the sample may be ascertained.

A convenient means for carrying out the method of the invention is to provide an immunological diagnostic kit comprising a piezoelectric oscillator having an antigen adsorbed thereon. In conjunction with the antigen-/oscillator composite, there is provided one or more reagents, at least one of which is an excess amount of a substance specifically reactive with antibody bound to the primary antigen layer. When performing competitive binding assays for antigen, a predetermined amount of the antibody specific for the antigen adsorbed on the crystal is also supplied in the kit.

The sandwich assay of the present invention is useful to determine the amount of antibody attached to the crystal in any situation involving nonspecific binding of extraneous substance to the primary antigen layer. It is especially useful in competitive assays of small molecules. Examples of small molecules of clinical interest present in patient sera or urine include: vitamins, co-factors, hormones, polypeptides, prostaglandins, cyclic nucleotides, antibiotics and other drugs, sugars, and many other metabolites of host or infectious organisms.

The antibody reagents necessary to perform a competitive binding assay for small molecules are generally obtained by conjugating the small molecule as a hapten to an antigenic protein or synthetic polypeptide carrier prior to injection into a host animal. Methods of synthesizing such hapten-protein or hapten-polypeptide conjugates are well known in the art. Animals immunized with the conjugates usually form antibodies capable of specifically binding the unconjugated molecule.

The sandwiching reagent which binds specifically to the antibody on the crystal is preferably obtained immunologically by injection of the antibody into a host animal. Antibodies to the antibody or anti-antibodies are obtained in the conventional manner.

The sandwiching assay of the present invention will be further understood by reference to the following illustrative example involving the measurement of testosterone.

EXAMPLE

The procedure followed for the indirect assay for testosterone begins with the cleaning of a 5 Hz quartz crystal oscillator. The crystal is cleaned either by immersion in a 10% aqueous solution of trisodium phosphate for 1 hour at 20° C. with subsequent rinsing in distilled water or by immersion in trichloroethylene for 30 seconds followed by 5 consecutive rinses of 5 seconds each in distilled water with subsequent immersion in an ultrasonic bath containing 190 proof ethanol for 15 to 45 minutes and drying under a stream of dry nitrogen gas. The crystal is then treated with the primer poly(2-hydroxy-3-dimethylamino-1,4 butane) (DIMA) by immersion in an 0.08% aqueous solution thereof for 18 hours at 20° C. Following rinsing with distilled water, the crystal is dried. Subsequently, the crystal is immersed in a solution (1 mg/ml in 0.1 M phosphate buffer pH 7.2) of testosterone, conjugated to keyhole limpet hemocyanin (testosterone-KLH) (see *Methods in Enzymology* Volume XXXVI "Hormone Action," Part A, Steroid Hormones, Edited by O'Malley and Hardman, Academic Press, 1975, p. 21). After a 4-hour incubation period at room temperature, the crystal is washed, dried and the frequency ($\Delta Hz$) measured. The antibody, rabbit antitestosterone-BSA, (Cappel Labs) is produced in rabbits that had been injected with testosterone conjugated to bovine serum albumin (BSA). The antitestosterone-BSA is mixed with human sera samples titered for testosterone by a radioimmunoassay (RIA) method. In the sandwich assay of the present invention, there is no need for any prior organic separation or treatment of the sera samples. The mixture of antitestosterone-BSA and the testosterone sera samples is incubated for 45 minutes at 37° C. A 0.05 ml aliquot of the mixture is applied to the testosterone-KLH coated crystal. After a 75-minute incubation at room temperature, the crystal is washed, dried and the frequency determined. The principle of this indirect or competitive inhibition assay is that the antitestosterone-BSA + testosterone (in the sera) complex prevents the subsequent binding of the complexed antitestosterone-BSA to the testosterone-KLH coated crystal. Therefore, the binding of the free antibody to the antigen-coated crystal is inversely proportional to the amount of testosterone in the sera sample. As seen in Table 1, Column A, the antitestosterone binding or $\Delta Hz$ has no relationship to the amount of testosterone used as the inhibitor. This can be explained by serum proteins non-specifically binding to the crystals and masking the specific antibody binding.

To overcome the effect of the nonspecific binding and to determine the amount of antitestosterone bound to the crystal, a second antibody is used. The second antibody, sheep anti-rabbit IgG from Cappel Labs, will only bind to the rabbit antitestosterone due to the species specificity of antibodies. 0.05 ml of the anti-rabbit IgG at 0.85 mg/ml in 0.1 M phosphate buffered saline pH 7.2 was applied to the crystal and incubated for 75 minutes at room temperature. The crystal was then washed, dried and the frequency measured. As seen in Table 1, Column B, the change in frequency ($\Delta Hz$) of the second antibody, anti-IgG, correlates well with the RIA testosterone titers. The correlation coefficient (r) equals 0.93.

TABLE 1

| Inhibition Sample µg/ml Testosterone | A $\Delta Hz$ Post Anti-testosterone | B $\Delta Hz$ Post Anti-IgG |
|---|---|---|
| 13.57 | 150 | 136 |
| 6.79 | 110 | 187 |
| 3.40 | 88 | 200 |
| 1.70 | 89 | 224 |
| 0.85 | 72 | 274 |
| 0.21 | 93 | 277 |
| 0 (antibody alone) | 70 | 342 |
| Sera alone | 94 | 17 |

Correlation Coefficient (r)
Column A = 0.77
Column B = 0.93

What is claimed is:

1. In a method for determining the total amount of an immunologically-reactive substance in a liquid sample containing interfering material capable of binding to an antigen comprising the steps of: (1) contacting a liquid sample containing or suspected of containing an antibody with the surface of a piezoelectric oscillator having a layer of antigen specific for said antibody attached thereto; (2) washing and drying said oscillator; and (3) measuring the resonance frequency of said oscillator, the improvement comprising the further steps of: (4) contacting said surface of said oscillator with a liquid reagent containing an excess amount of a substance specifically reactive with all of said antibody bound to said oscillator in step (1); (5) washing and drying said oscillator; and (6) measuring the change in resonance frequency of said oscillator from said first measurement whereby the amount of total antibody bound to said oscillator in step (1) is distinguished from said interfering material bound in said step (1).

2. The method according to claim 1 wherein said liquid sample in step (1) contains a predetermined amount of said antibody and is suspected of containing the same antigen attached to said oscillator.

3. The method according to claim 2 wherein said antigen is a low molecular weight material.

4. The method according to claim 3 wherein said antigen is testosterone.

5. The method according to claims 1 or 2 wherein said reactive substance in step (4) is an anti-antibody.

6. The method according to claim 1 wherein said oscillator is a quartz crystal.

7. The method according to claim 1 wherein said oscillator has adsorbed thereon a monolayer of poly(2-hydroxy-3-dimethylamino-1,4 butane) to which is attached said antigen layer.

8. A diagnostic test kit for the quantitative determination of the total amount of an immunologically-reactive substance in a liquid sample containing interfering material capable of binding to an antigen comprising:

a piezoelectric oscillator having a layer of antigen attached thereto; and a reagent containing an excess amount of a substance reactive with all of the antibody reactive with said antigen.

9. The kit according to claim 8 further comprising a second reagent containing a predetermined amount of antibody specific for said antigen.

10. The kit according to claim 8 and 9 wherein said reactive substance is an anti-antibody.

11. The kit according to claim 9 wherein said antigen is a small molecule.

12. The kit according to claim 11 wherein said small molecule is testosterone.

* * * * *